(12) United States Patent
Heuser (10) Patent No.: US 7,166,088 B2
(45) Date of Patent: Jan. 23, 2007

(54) CATHETER INTRODUCER SYSTEM

(76) Inventor: Richard R. Heuser, 525 N. 18th St., Suite 504, Phoenix, AZ (US) 85006

( * ) Notice: Subject to any disclaimer, the term of this patent is extended or adjusted under 35 U.S.C. 154(b) by 308 days.

(21) Appl. No.: 10/352,326

(22) Filed: Jan. 27, 2003

(65) Prior Publication Data

US 2004/0147877 A1    Jul. 29, 2004

(51) Int. Cl.
*A61M 5/178* (2006.01)
(52) U.S. Cl. .................................. 604/164.1
(58) Field of Classification Search ........... 604/164, 604/165, 166, 170, 171, 523–539, 264–279
See application file for complete search history.

(56) References Cited

U.S. PATENT DOCUMENTS

| | | | |
|---|---|---|---|
| 3,788,318 A * | 1/1974 | Kim et al. ............. | 604/164.03 |
| 4,000,739 A | 1/1977 | Stevens | |
| 4,634,342 A | 1/1987 | Rodewald | |
| 4,634,432 A | 1/1987 | Kocak | |
| 4,650,472 A | 3/1987 | Bates | |
| 4,682,981 A | 7/1987 | Suzuki et al. | |
| 4,705,511 A | 11/1987 | Kocak | |
| 4,862,891 A * | 9/1989 | Smith ..................... | 606/191 |
| 4,874,378 A | 10/1989 | Hillstead | |
| 4,895,564 A * | 1/1990 | Farrell ................... | 604/164.1 |
| 4,950,257 A * | 8/1990 | Hibbs et al. ........... | 604/265 |
| 5,092,846 A | 3/1992 | Nishijima et al. | |
| 5,147,336 A * | 9/1992 | Wendell et al. ........ | 604/533 |
| 5,242,410 A * | 9/1993 | Melker .................. | 604/164.1 |
| 5,256,158 A * | 10/1993 | Tolkoff et al. ......... | 604/529 |
| 5,257,979 A | 11/1993 | Jagpal | |
| 5,267,966 A | 12/1993 | Paul | |
| 5,290,310 A * | 3/1994 | Makower et al. ...... | 606/213 |
| 5,292,311 A | 3/1994 | Cope | |
| 5,380,304 A | 1/1995 | Parker | |
| 5,395,341 A | 3/1995 | Slater | |
| 5,423,774 A | 6/1995 | Fischell et al. | |
| 5,466,230 A | 11/1995 | Davila | |
| 5,499,975 A | 3/1996 | Cope et al. | |
| 5,514,236 A | 5/1996 | Avellanet et al. | |

(Continued)

*Primary Examiner*—Manuel Mendez
(74) *Attorney, Agent, or Firm*—Kolisch Hartwell, P.C.

(57) ABSTRACT

A catheter introducer system is provided with a catheter sheath having a valve providing for a friction fit around a catheter. The friction fit is selectively adjustable to vary between a first configuration for longitudinal movement of the catheter through the valve and a second configuration for holding the catheter longitudinally in place. The valve may includes a chuck to grip the catheter radially. The chuck may include an annular base and an opposed annular clamp, and a washer disposed between the base and the clamp. At least one of the base and the clamp may include a beveled surface that forces the washer radially inwardly as the base and the clamp are drawn together. The system also includes one or more dilators layered within the sheath. The layered dilators and sheaths are typically softer and more hydrophilic proceeding from the innermost dilator out to the sheath. The dilator may be reinforced by a wire embedded in the body of the dilator. The distal tip of the sheath may be stiffened by a ring affixed adjacent the distal end. The sheath may include in the innermost dilator a trocar formed of a flexible, hollow outer wire and an inner stiff needle, which can extend beyond the wire for piercing and be withdrawn to relax the wire for advancement of the dilator.

10 Claims, 6 Drawing Sheets

U.S. PATENT DOCUMENTS

| | | | |
|---|---|---|---|
| 5,591,137 A * | 1/1997 | Stevens | 604/296 |
| 5,599,325 A * | 2/1997 | Ju et al. | 604/524 |
| 5,707,359 A * | 1/1998 | Bufalini | 604/104 |
| 5,807,350 A | 9/1998 | Diaz | |
| 5,820,607 A | 10/1998 | Tcholakian et al. | |
| 5,897,497 A | 4/1999 | Fernandez | |
| 5,911,710 A * | 6/1999 | Barry et al. | 604/249 |
| 5,989,223 A * | 11/1999 | Chu et al. | 604/167.05 |
| 6,004,310 A * | 12/1999 | Bardsley et al. | 604/524 |
| 6,022,343 A * | 2/2000 | Johnson et al. | 604/526 |
| 6,245,052 B1 * | 6/2001 | Orth et al. | 604/506 |
| 6,283,958 B1 * | 9/2001 | Vogl et al. | 606/15 |

* cited by examiner

CATHETER INTRODUCER SYSTEM

BACKGROUND

Catheters typically are inserted into a blood vessel through a sheath which is fixed in place relative to the blood vessel. The sheath protects the vessel and adjacent derma around the point of insertion while the catheter is advanced and withdrawn as necessary for the particular treatment being applied. The sheath is prepared for insertion by first placing a dilator within the lumen of the sheath and a needle or pointed wire within the lumen of the dilator. The needle or wire is used to pierce the derma and the blood vessel's wall and then is advanced into the blood vessel's lumen. Then the dilator is advanced along the wire without moving the needle or wire so that the tip of the dilator passes through the derma and blood vessel wall, expanding the diameter of the opening into the blood vessel.

At this point, with the dilator tip within the blood vessel lumen, the needle or wire may be withdrawn from the blood vessel. The sheath may then be advanced along the dilator, holding the dilator stationary, until the tip of the sheath is within the blood vessel's lumen. The sheath typically also expands the opening into the blood vessel. Once the sheath is in the blood vessel at a suitable location, the dilator may be withdrawn and the sheath braced in position, for example by taping the sheath to the patient's arm or leg adjacent the point of insertion. Then, the catheter is inserted through the sheath and into the blood vessel and maneuvered as necessary to provide the desired treatment.

The catheter's outer diameter (o.d.) in such a system is limited by the inner diameter of the sheath, which in turn is limited by the expansion provided by the dilator. A typical dilator-sheath introducer provides a dilator lumen allowing only a 3-French or 0.038 inch o.d. wire, and the dilator must be expand outwardly relatively abruptly to reach even a modest outer diameter. The sheath lumen then is the same size as the outer diameter of the dilator, and typical size is only a 9-French or 0.118 inch, thus limiting the o.d. of the catheter to 9-French, which limits the types and capabilities of the catheters that can be used with such an introducer.

The dilator and sheath are typically formed of a plastic material and the tips of the dilator and sheath are sometimes damaged by insertion into the blood vessel. This may cause trauma to the derma and blood vessel, or require a second needle insertion if the tip is damaged to the extent it prevents suitable insertion.

The sheath typically includes an elastic collar adjacent a proximal end, through which the catheter is inserted. Such elastic collars are typically designed to allow the catheter to be advanced and withdrawn while providing some deterrence to blood leaking out through the sheath between the washer and the catheter. However, blood leakage past the washer is sometimes significant, causing unwanted complications to the catheterization procedure.

SUMMARY

A catheter introducer system is provided for inserting a sheath into a human blood vessel to provide a channel for a catheter to be moved within the blood vessel and to be held in a fixed position with minimum blood loss through the sheath. The catheter introducer system may include a trocar or other pointed instrument, such as a needle or pointed wire, for initially piercing the derma and the wall of the blood vessel. One or more dilators may surround the trocar and be sequentially inserted into the blood vessel after the trocar. The sheath surrounds the outermost of the dilators and is inserted last into the blood vessel. After removal of the trocar and dilator(s), the catheter may be inserted into the sheath and maneuvered within the blood vessel as necessary for the desired treatment.

When the catheter is at a desired location, it may be fixed longitudinally in place and blood loss through the sheath minimized by selective tightening of a hemostasis valve that includes a chuck that radially grips the catheter. The chuck may include a washer held between a base and a clamp and tightened therebetween, with beveled surfaces on the base, clamp, and/or the washer to provide for radial tightening of the chuck on the catheter.

DETAILED DESCRIPTION OF THE PREFERRED EMBODIMENTS

Figure 1:
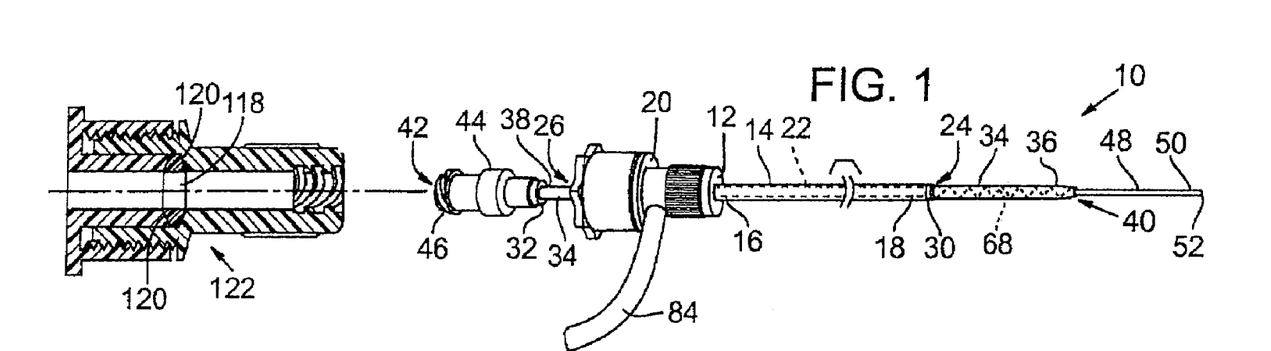
FIG. 1 is an isometric view of a catheter introducer system according to the present invention, including a dilator, a sheath, and a trocar.

A catheter introducer system in accordance with the present invention is indicated generally at 10 in FIG. 1. Catheter introducer system 10 includes a sheath 12 having a generally elongate, typically cylindrical body 14 with a proximal end 16 and a distal end 18. Body 14 of sheath 12 is coupled at proximal end 16 to a housing 20. A central, typically cylindrical lumen 22 is defined within sheath 12 extending out through a distal opening 24 and a proximal opening 26. Sheath 12 is thus configured to receive a catheter 28 (FIG. 5) for longitudinal movement through and torsional movement within lumen 22.

Body 14 of sheath 12, is typically composed substantially of a flexible material, such as a plastic, polymeric material, preferably a hydrophilic material. Body 14 may include a reinforcement, such as stainless steel ring 30, to prevent buckling or crimping of distal end 18 at opening 24 when sheath 12 is inserted into a human blood vessel. The stainless steel ring 30 on the outermost sheath is radiopaque, as would be understood by those of ordinary skill in the art.

Catheter introducer system 10 further includes a first dilator 32 configured to be inserted into and disposed substantially within lumen 22 of sheath 12. First dilator 32 includes a generally elongate, typically cylindrical body 34 having a distal end 36 and a proximal end 38. Dilator 32 typically also includes a lumen interconnecting a distal opening 40 and a proximal opening 42, which typically is located in a housing 44 coupled to body 34 adjacent proximal end 38. Housing 44 may be provided with a luer lock fitting 46, which typically includes a double threaded engagement portion for coupling to mating devices.

Sheath 12 and dilator 32 typically are generally cylindrical, as noted above, typically with tapering adjacent distal ends 18, 36 to provide a smooth transition as the ends enter the blood vessel. Alternatively sheath 12 and dilator 32, and one or more intermediate dilators (to be described below), may be tapered substantially along the entire length of their bodies, preferably providing a more gradual, or additional, tapering as compared to the tapered distal ends. In either case, the sheath and dilators are preferably provided with a smooth transition between the body of one dilator and the distal end of the next outer sheath or dilator to prevent the distal end from snagging on the derma or blood vessel during insertion into the blood vessel.

Dilator 32 is preferably longer than sheath 12 so that distal end 36 and proximal end 38 of body 34 of dilator 32 extend out of the distal and proximal openings of sheath 12, as shown in FIG. 1. As an example, dilator 32 may be on the order of about 24 cm long and sheath 12 may be in the range of about 16 cm to about 20 cm, with other lengths selectable as appropriate for a particular application.

Catheter introducer system 10 may also include a trocar 48 inserted through dilator 32 and including a distal end 50 with a sharp, pointed tip 52. Trocar 48 is inserted through dilator 32 to create the initial entrance through the derma and into the blood vessel, and trocar 38 then is withdrawn after distal end 36 of dilator 32 is advanced into the blood vessel.

Figure 2:
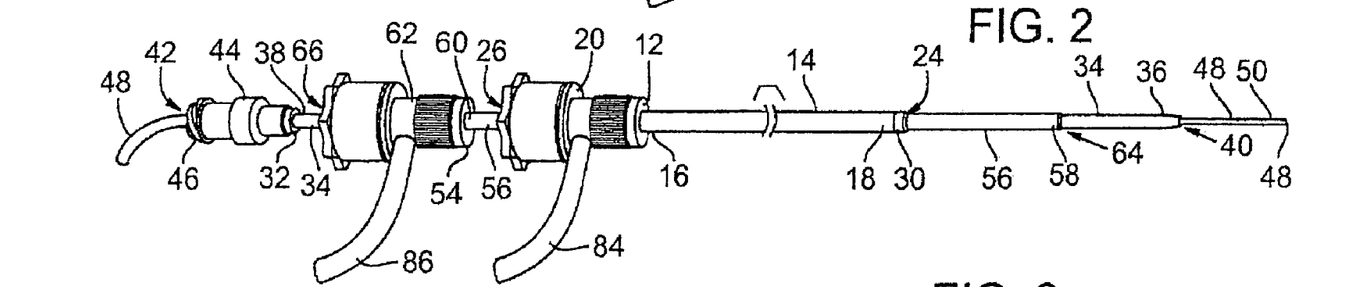
FIG. 2 is an isometric view of the catheter introducer system as shown in FIG. 1, the system in this embodiment including two dilators.

As shown in FIG. 2, catheter introducer system 10 may include a second, intermediate dilator 54 between the first dilator 32 and sheath 12. Second dilator 54 typically includes a generally elongate, substantially cylindrical body 56 with a distal end 58 and a proximal end 60. A housing 62 is coupled to body 56 adjacent proximal end 60. A central lumen, similar to that for sheath 12 and first dilator 32 interconnects a distal opening 64 and a proximal opening 66.

Second dilator 54 preferably has a length greater than that of sheath 12 and less than that of first dilator 32. Thus, if first dilator 32 is about 24 cm, second dilator 54 is about 20 cm and sheath 12 is about 16 cm in length. The lengths of all the components of the catheter introducer system may be adapted for the particular application.

Preferably the dilator(s) and sheath are formed of less stiff, more flexible material as one progresses from innermost to outermost. E.g., first dilator 32 may be formed with the most stiff material, and may include a reinforcement, such as a wire 68 (FIG. 1), embedded or otherwise affixed to the material in a coil, web, or other suitable pattern to provide a stiffener. Second dilator 54 is typically formed of a less stiff material, while sheath 12 is formed of a still softer material so that the sheath/dilator bodies tend to be less traumatic to the blood vessel as they get larger. Second dilator, and other intermediate dilators, and sheath are typically progressively more hydrophilic as one proceeds outwardly. Ring 30, described above, helps to insure that the soft material of sheath 12 will not buckle or flare if the sheath tip catches or snags on the derma on insertion into the blood vessel. A ring may also be provided on the tips of one or more of the dilators in addition to or instead of on sheath 12.

With a two-dilator/one-sheath system, some typically available inner diameters (i.d.) in French sizes are shown in the following table:

| Two-dilator/ one-sheath | First dilator i.d. | Second dilator i.d. | Sheath i.d. |
|---|---|---|---|
| Ex. 1 | 3 | 4 | 5 |
| Ex. 2 | 3 | 5 | 6 |
| Ex. 3 | 3 | 5 | 7 |
| Ex. 4 | 3 | 5 | 8 |
| Ex. 5 | 3 | 5 | 9 |
| Ex. 6 | 3 | 8 | 16 |

Other sizes may be used as appropriate for a particular application.

Figure 3:
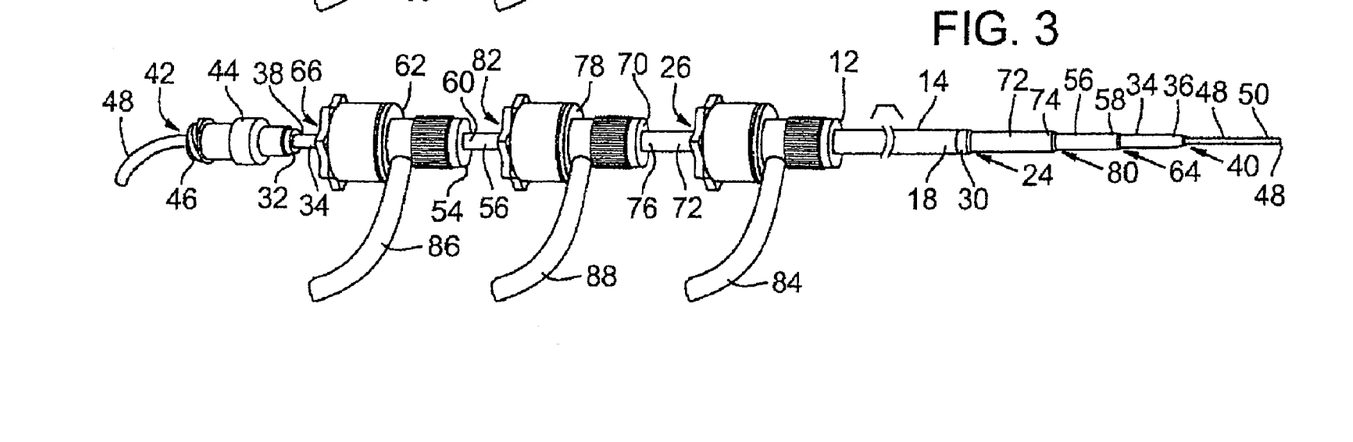
FIG. 3 is an isometric view of the catheter introducer system as shown in FIGS. 1 and 2, the system in this embodiment including three dilators.

As shown in FIG. 3, catheter introducer system 10 may include a third, intermediate dilator 70 between the second dilator 54 and sheath 12. Second dilator 70 typically includes a generally elongate, substantially cylindrical body 72 with a distal end 74 and a proximal end 76. A housing 78 is coupled to body 72 adjacent proximal end 76. A central lumen, similar to that for the sheath and the first and second dilators interconnects a distal opening 80 and a proximal opening 82.

Third dilator 70 is preferably intermediate in length, in softness, and in hydrophilicity between second dilator 54 and sheath 12. With a three-dilator/one-sheath system, some typically available inner diameters (i.d.) in French sizes are shown in the following table:

| Three-dilator/ one-sheath | First dilator i.d. | Second dilator i.d. | Third dilator i.d. | Sheath i.d. |
|---|---|---|---|---|
| Ex. 7 | 3 | 5 | 7 | 10 |
| Ex. 8 | 3 | 5 | 9 | 11 |
| Ex. 9 | 3 | 5 | 9 | 12 |
| Ex. 10 | 3 | 5 | 9 | 13 |
| Ex. 11 | 3 | 5 | 9 | 14 |
| Ex. 12 | 3 | 5 | 9 | 15 |
| Ex. 13 | 3 | 5 | 9 | 16 |
| Ex. 14 | 3 | 5 | 9 | 17 |
| Ex. 15 | 3 | 5 | 9 | 18 |

Other sizes may be used as appropriate for a particular application.

It will be seen from the foregoing that the system may include any number of dilators to reach a desired sheath size, and, for example, a four-dilator/one-sheath system could use the following sizes:

| Four-dilator/<br>one-sheath | First<br>dilator i.d. | 2nd<br>dilator i.d. | 3rd<br>dilator i.d. | 4th<br>dilator i.d. | Sheath<br>i.d. |
|---|---|---|---|---|---|
| Ex. 16 | 3 | 5 | 9 | 12 | 19 |
| Ex. 17 | 3 | 5 | 9 | 12 | 20 |
| Ex. 18 | 3 | 5 | 9 | 12 | 21 |
| Ex. 19 | 3 | 5 | 9 | 12 | 22 |
| Ex. 20 | 3 | 5 | 9 | 12 | 23 |
| Ex. 21 | 3 | 5 | 9 | 15 | 24 |
| Ex. 22 | 3 | 5 | 9 | 15 | 26 |
| Ex. 23 | 3 | 5 | 9 | 15 | 28 |

Other sizes may be used as appropriate for a particular application.

Sheath 12 as shown in FIGS. 1–3 includes a side branch or arm 84 in housing 20, which is commonly used for the introduction of intravenous fluid or medicine during a catheterization procedure. As shown in FIGS. 2 and 3, second dilator 54 includes a side branch 86 in housing 62 and third dilator 70 includes a side branch 88 in housing 78. Although the term dilator is commonly used to refer to a device without a side branch, FIGS. 2 and 3 illustrate that dilator, as used herein, can refer to a device either with or without a side branch, and the catheter introducer system may be used with sheaths and dilators including any combination of side branches or lack thereof.

Figure 4:
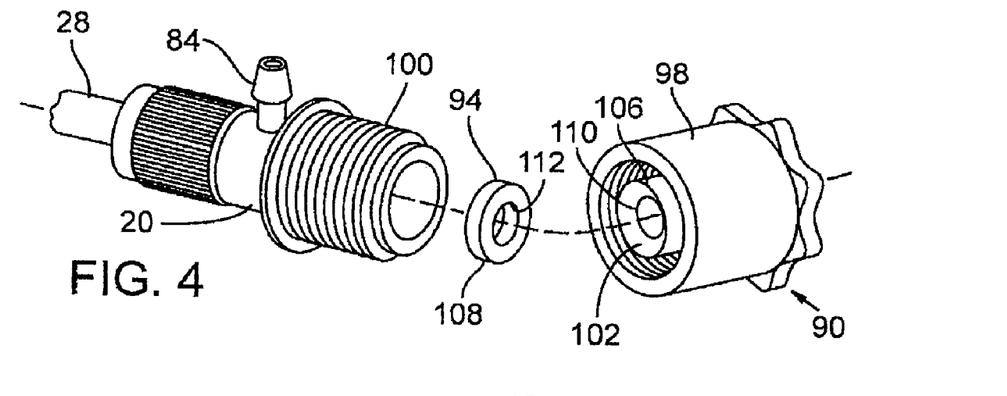
FIG. 4 is an isometric, exploded view of a proximal end of a sheath in accordance with the present invention, including a hemostasis valve with a chuck for variably gripping a catheter, the chuck including a base, a clamp coupled to the base by a threaded engagement, and a washer disposed between the base and the clamp.
Figure 5:
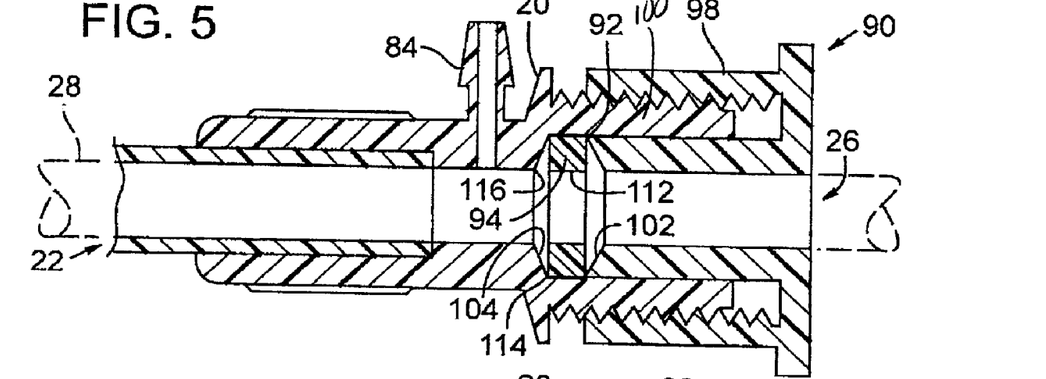
FIG. 5 is a cross-sectional view of the proximal end of the sheath shown in FIG. 4, with the catheter inserted through the sheath and the washer therein, the clamp positioned to allow the catheter to move longitudinally through the sheath.
Figure 6:
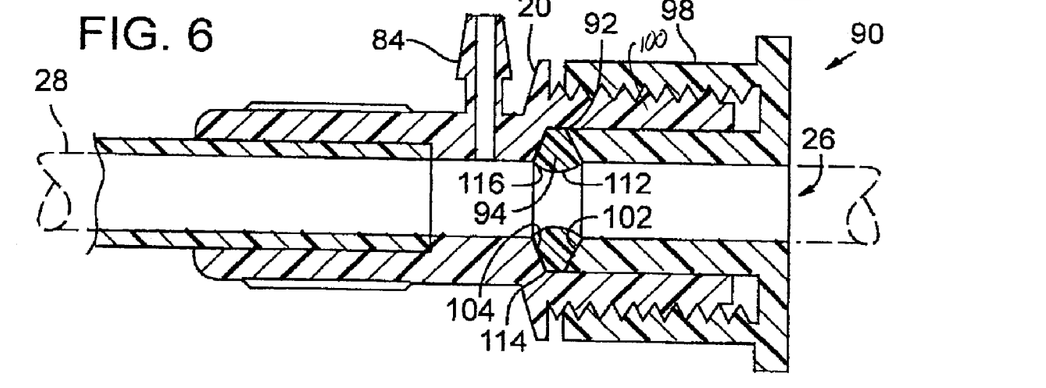
FIG. 6 is a cross-sectional view of the sheath as in FIG. 5, with the clamp positioned to tighten the washer onto the catheter.

As best seen in FIGS. 4–6, housing 20, which may be identical in the following respects to the housings on any or all of the dilators, includes a hemostasis valve, indicated generally at 90, for preventing blood leaks between catheter 28 and housing 20. Such blood leaks typically flow along inner lumen 22 and out proximal opening 26. Housing 20 is shown in FIGS. 4–6 with all of the smaller dilators and the trocar withdrawn, and, in FIGS. 5 and 6 with catheter 28 inserted.

Hemostasis valve 90 includes a chuck 92 for selectively gripping radially onto catheter 28. Chuck 92 includes a collar, such as flexible, elastomer washer 94, defining an opening 96 configured to receive catheter 28 therethrough. Preferably washer 94 fits snugly around catheter 28 in a first configuration, shown in FIG. 5, allowing catheter 28 to be moved longitudinally therethrough.

Valve 90 thus provides for a friction fit around the catheter. The friction fit is selectively adjustable to vary between a first configuration for longitudinal movement of the catheter through the valve and a second configuration for holding the catheter longitudinally in place. A physician operating the catheter introducer system may selectively switch valve 90 to the second configuration, typically when catheter 28 is in a desired location within the blood vessel to perform a catheter procedure, such as installing a stent or applying RF energy at the distal tip of the catheter.

Preferably the physician selects the second configuration by grasping a threaded cap 98 of valve 90, and rotating to tighten cap 98 onto a threaded portion 100 of housing 20. Such tightening of cap 98 drives a clamp 102 within cap 98 to squeeze washer 94 between clamp 102 and a base 104 in housing 20. Preferably, clamp 102 is a sloped annular ring providing a beveled surface within cap 98. The ring preferably has an outer circumference 106 generally coincident with an outer circumference of washer 92, and an inner circumference 110 generally coincident with an inner circumference 112 of washer 92. Preferably, base 104 is a sloped annular ring, providing a beveled surface that includes an outer circumference 114 and an inner circumference 116 coincident with corresponding circumferences of the washer and the clamp. Inner circumference 112 of washer 92 is nominally at least as large as the o.d. of catheter 28, although it can be smaller to provide a tighter nominal friction fit.

In the second configuration, shown in FIG. 6, cap 98 has been tightened onto housing 20 so that clamp 102 and base 104 are closer together than a nominal width of washer 92. Thus washer 92 is pressed radially inwardly by the sloping faces of clamp 102 and base 104, which tends to reduce the washer's inner circumference 112 and to close opening 96, thereby tightening washer 92 onto catheter 28. Valve 90 may be selectively adjusted by the physician to any degree of tightness, thereby allowing the physician to select an optimal combination of leakage prevention and ease of catheter longitudinal and torsional movement. Preferably, with cap 98 fully tightened, substantially no blood leaks between catheter 28 and washer 92 and catheter 28 is substantially locked longitudinally in place.

Washer 92 is shown in FIGS. 4–6 as a flat washer. Washer 92 may alternatively have one or two sloped or beveled surfaces which may correspond to the sloped faces of clamp 102 and base 104. A washer 118 with two sloped faces 120 is shown in FIG. 1 incorporated into a hemostasis valve, indicated generally at 122, on first dilator 32. Valve 122 operates in a manner generally similar to that of valve 90.

Figure 7:
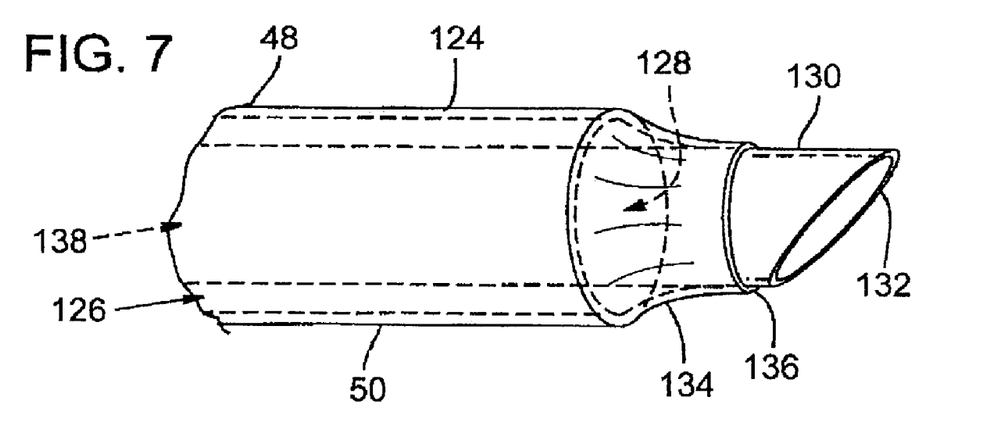
FIG. 7 is a close-up pictorial view of the distal tip of the trocar of the catheter introducer system, showing an outer, hollow wire, an inner needle within the lumen of the wire and including a beveled tip extending out of the wire, and a boot at the tip of the wire.

FIGS. 7–14 show embodiments of trocar 48, in particular the structure at distal end 50 of trocar 48. Trocar 48 may include a hollow, preferably flexible wire 124 defining a central lumen 126 extending out to a distal opening 128. A hollow, preferably stiff needle 130 provided with a sharp tip, such as beveled end 132, may be inserted in lumen 126. In an operative condition, as shown in FIG. 7, tip 132 will extend out of opening 128 of wire 124. A sealing mechanism, such as flexible cuff or boot 134 may be coupled to wire 124 at opening 128. Sealing mechanism 134 includes an opening 136 which stretches to allow needle tip 132 to extend through the sealing mechanism in the operative condition. Needle 130 includes a proximal end extending out of the proximal end of trocar 48, which extends out of proximal opening 42 of dilator 32 (see FIGS. 1–3). Needle 130 also includes a central lumen 138 extending from tip 132 to the proximal end.

Figure 13:
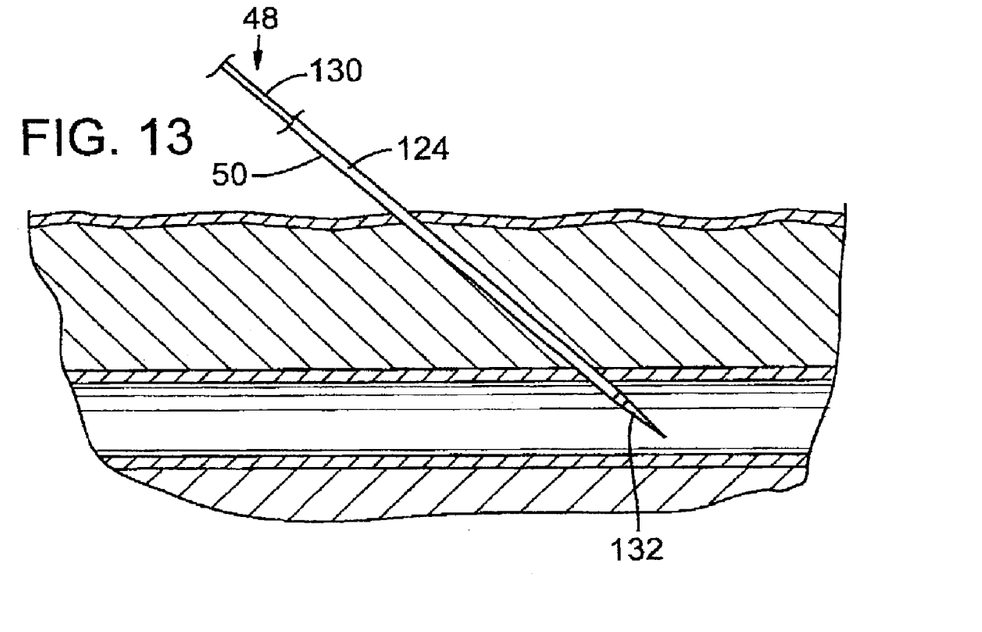
FIG. 13 is a side, cross-sectional view of the trocar of FIGS. 7–12 with the needle and wire tip inserted through the derma and into the blood vessel lumen of the patient, with the needle tip still extending out of the distal opening of the wire.
Figure 14:
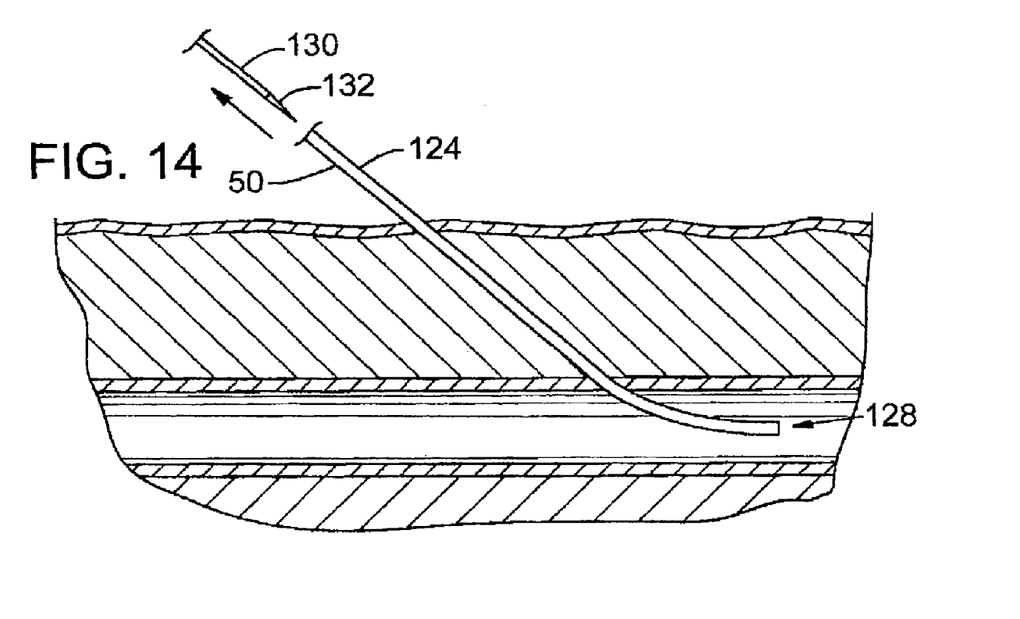
FIG. 14 is a side, cross-sectional view of the trocar as in FIG. 13 with the needle withdrawn from the wire and the wire returned to a flexible state within the blood vessel lumen.

As shown in FIGS. 13 and 14, the physician may use trocar 48 with needle tip 132 extending out of wire 124 to insert the trocar tip through the patient's derma and into the blood vessel. FIG. 13 shows that the flexible wire with the stiff needle inserted therethrough is stiff and insertable into the blood vessel along with the needle tip. The physician can verify that the needle tip is in the blood vessel by the blood that will flow into lumen 138 of needle 130 and out the proximal end.

Figure 8:
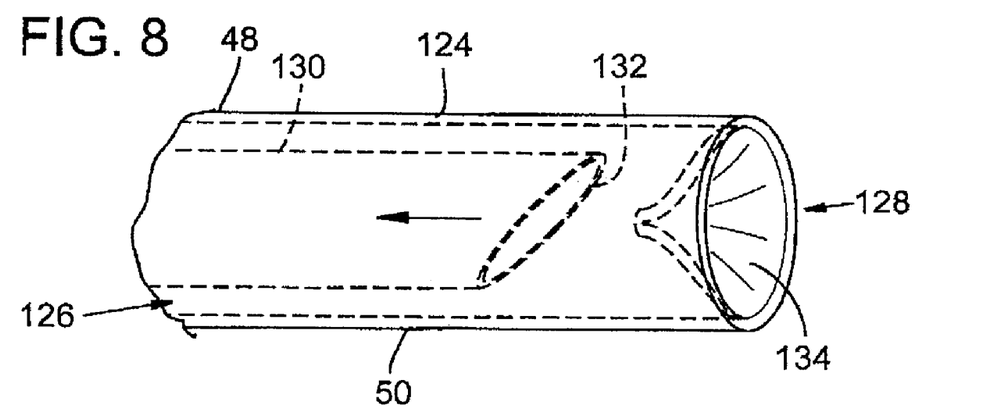
FIG. 8 is a pictorial view of the trocar of FIG. 7 with the inner needle withdrawn into the wire and the boot closing to seal off the lumen of the wire.

Once the wire and needle are verified as inserted into the lumen of the blood vessel, the physician can pull on the proximal end of the stiff needle, withdrawing it from the trocar tip, as shown in FIG. 14, at which time wire 124 will again become flexible. The flexible wire presents a less dangerous and traumatic device within the blood vessel, as compared to a stiff wire or needle. The withdrawn needle is also shown in FIG. 8, where it can be seen that sealing mechanism 134 has closed to prevent further blood flow through trocar 48.

Figure 9:
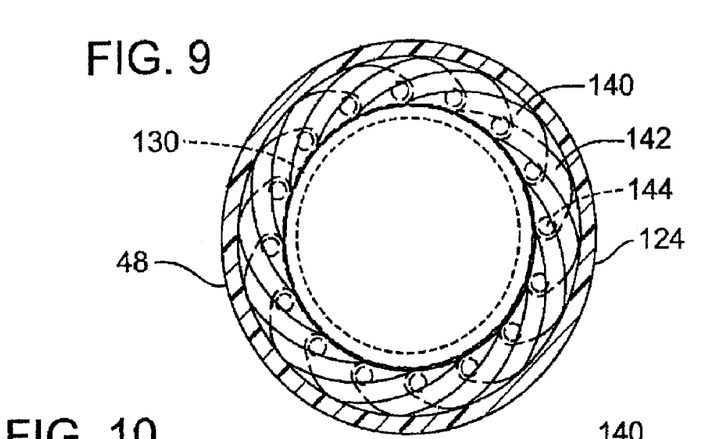
FIG. 9 is a close-up end view of an alternative embodiment of the trocar of the catheter introducer system, showing a shutter at the tip of the wire that is open and a needle within the opening of the shutter.
Figure 10:
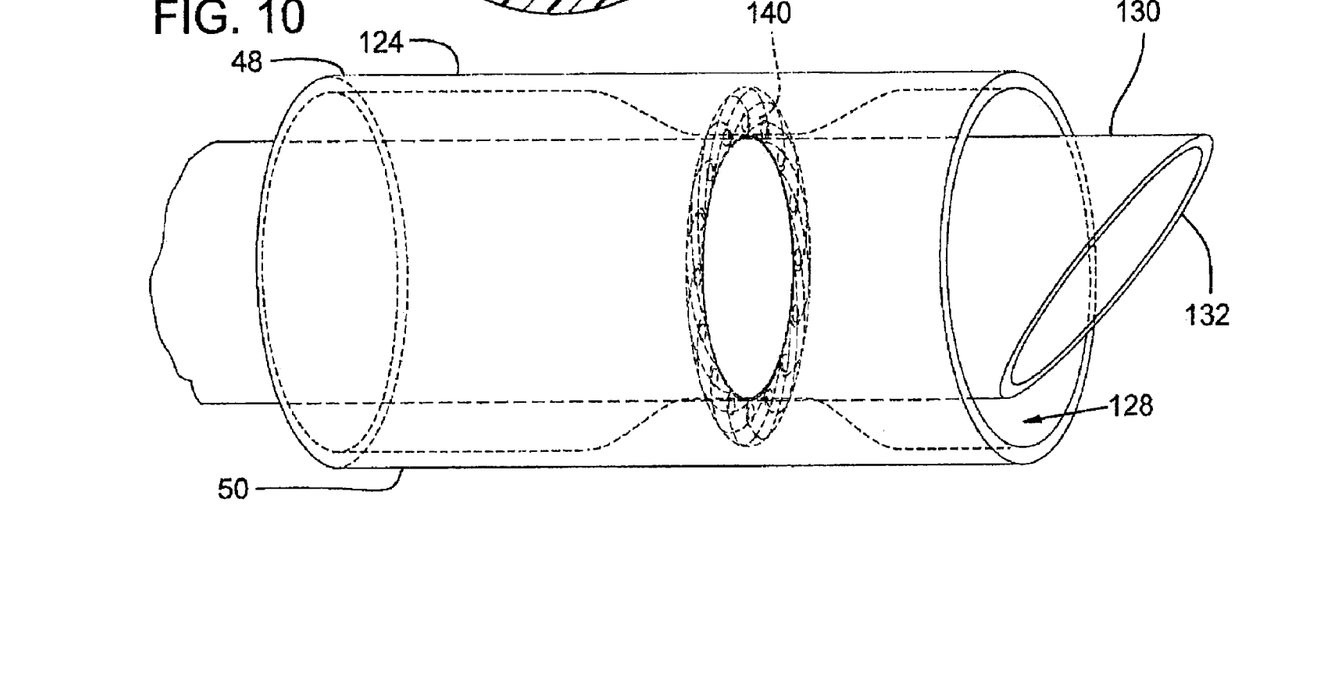
FIG. 10 is a pictorial view of the trocar in the extended configuration shown in FIG. 9.
Figures 11, 12:
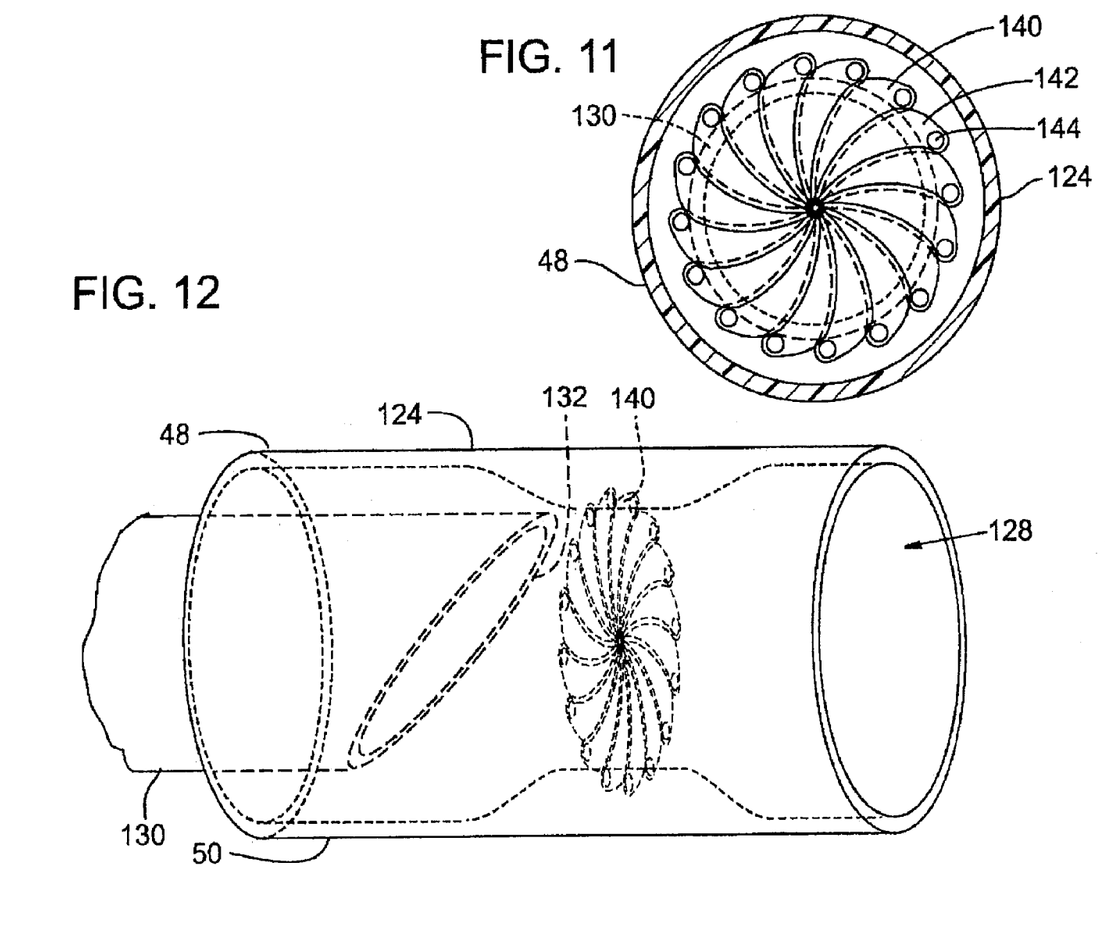
FIG. 11 is an end view of the trocar of FIG. 9 with the needle withdrawn into the wire and the shutter closed.
FIG. 12 is a pictorial view of the trocar in the withdrawn configuration of FIG. 11.

Another embodiment of a sealing mechanism is shown in FIGS. 9–12, where wire 124 includes adjacent opening 128 a shutter 140. A plurality of shutter vanes 142 may be mounted on hinges 144 and preferably may be nominally biased to a closed position (FIGS. 11 and 12). Shutter 140 can be opened by inserting tip 132 of needle 130 through the shutter, as is shown in FIGS. 9 and 10. The physician uses the embodiment of FIGS. 9–12 in the same manner as that of FIGS. 7 and 8, inserting the needle tip through the derma and into the lumen of the blood vessel and then withdrawing the needle, allowing the shutter to close and the wire 124 to go limp, as shown in FIGS. 13 and 14.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. No single feature, function, element or property of the disclosed embodiments is essential to all of the disclosed inventions. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also included within the subject matter of the inventions of the present disclosure.

I claim:

1. A catheter introducer system for introduction of a catheter into a human blood vessel, the system comprising:
    a catheter sheath defining a generally elongate body with a lumen and distal and proximal openings communicating with the lumen and configured for insertion and longitudinal movement of the catheter therethrough;
    a first dilator defining a generally elongate body having a distal end and a proximal end, wherein the first dilator is disposed substantially within the lumen of the sheath, with the distal end of the first dilator extending through the distal opening of the sheath, the first dilator removable from the sheath for insertion of the catheter; and
    a trocar inserted through the lumen of the first dilator, the trocar including a flexible, hollow outer wire, wherein the wire is provided with sufficient flexibility and length for insertion into and safe passage along the human blood vessel for guidance of the catheter in the longitudinal movement of the catheter through the human blood vessel, and a stiff, inner needle with a distal end extending beyond a distal end of the wire, the needle configured for piercing through a patient's derma and entering the blood vessel.

2. The catheter introducer system of claim 1 wherein the needle of the trocar is hollow, and includes distal and proximal openings configured to allow blood to flow from the distal opening through to the proximal opening.

3. The catheter introducer system of claim 2 wherein the needle is beveled at the distal end to provide a derma-piercing point.

4. The catheter introducer system of claim 1 wherein the needle includes a proximal end extending out of a proximal end of the outer wire of the trocar, the proximal end configured to be grasped by a physician to withdraw the distal end of the needle.

5. The catheter introducer system of claim 4 wherein withdrawing the needle allows the outer wire to flex to conform to the human blood vessel.

6. The catheter introducer system of claim 4 wherein withdrawing the needle prevents further blood flow through the trocar.

7. The catheter introducer system of claim 6 wherein the hollow wire includes a valve adjacent the distal end of the wire.

8. The catheter introducer system of claim 7 wherein the valve is substantially closed by withdrawal of the needle.

9. The catheter introducer system of claim 8 wherein the valve includes a cuff that substantially closes on withdrawal of the needle.

10. The catheter introducer system of claim 8 wherein the valve includes a shutter that substantially closes on withdrawal of the needle.

* * * * *